US012799068B2

(12) United States Patent
Kordas et al.

(10) Patent No.: US 12,799,068 B2
(45) Date of Patent: Nov. 17, 2026

(54) METHOD FOR PRODUCING SECONDARY AND TERTIARY AMINES

(71) Applicant: HUNTSMAN PETROCHEMICAL LLC, The Woodlands, TX (US)

(72) Inventors: Imre Kordas, Veszprem (HU); Pietro Buono, Etterbeek (BE); Matthew T. Meredith, The Woodlands, TX (US); Heiko Heinrich Humbert, Hamburg (DE); Attila Gaspar, Petfurdo (HU); Petra Emma Vanderstraeten, Leuven (BE)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 583 days.

(21) Appl. No.: 18/035,144

(22) PCT Filed: Nov. 5, 2021

(86) PCT No.: PCT/US2021/058166

§ 371 (c)(1),
(2) Date: May 3, 2023

(87) PCT Pub. No.: WO2022/098940

PCT Pub. Date: May 12, 2022

(65) Prior Publication Data

US 2025/0333372 A1 Oct. 30, 2025

Related U.S. Application Data

(60) Provisional application No. 63/110,592, filed on Nov. 6, 2020.

(51) Int. Cl.
*C07C 213/02* (2006.01)
*C08G 18/18* (2006.01)

(52) U.S. Cl.
CPC ............ *C07C 213/02* (2013.01); *C08G 18/18* (2013.01)

(58) Field of Classification Search
None
See application file for complete search history.

(56) References Cited

U.S. PATENT DOCUMENTS

| | | | |
|---|---|---|---|
| 3,821,131 A | 6/1974 | Priest et al. | |
| 4,379,757 A | 4/1983 | Baskent et al. | |
| 5,420,170 A | 5/1995 | Lutter et al. | |
| 5,648,447 A | 7/1997 | Seneker et al. | |
| 5,756,558 A | 5/1998 | Savoca et al. | |
| 6,107,359 A | 8/2000 | Dietrich et al. | |
| 6,552,100 B2 | 4/2003 | McLaren et al. | |
| 6,737,471 B2 | 5/2004 | Lorenz et al. | |
| 6,790,872 B2 | 9/2004 | Kazmierski et al. | |
| 2010/0130715 A1 | 5/2010 | Grigsby, Jr. et al. | |
| 2012/0071622 A1* | 3/2012 | Gaspar .................. | C07C 217/08 528/53 |
| 2012/0130132 A1 | 5/2012 | Humbert et al. | |
| 2014/0155655 A1 | 6/2014 | Gaspar et al. | |

FOREIGN PATENT DOCUMENTS

| | | | |
|---|---|---|---|
| CN | 111205192 | A | 5/2020 |
| DE | 2618280 | A1 | 11/1977 |
| EP | 1505059 | A1 | 2/2005 |
| JP | 2005053913 | A | 3/2005 |
| JP | 2012-528815 | A | 11/2012 |
| JP | 2012528814 | A | 11/2012 |
| JP | 2013-544933 | A | 12/2013 |
| WO | 2010139520 | A1 | 12/2010 |
| WO | 2010139521 | A1 | 12/2010 |
| WO | 2012072441 | A1 | 6/2012 |
| WO | 2017160361 | A1 | 9/2017 |

OTHER PUBLICATIONS

European Written Opinion issued Sep. 20, 2024 in corresponding EP Application No. 21890112.2.
First Office Action issued Apr. 11, 2025, in corresponding Chinese Application No. 202180074781.7 (machine translation of the same enclosed herewith).
First Office Action issued Jul. 9, 2025, in corresponding Japanese Patent Application No. 2023-527299 (machine translation of the same enclosed herewith).
Office Action issued Jul. 29, 2026, in corresponding Japanese Patent Application No. 2023-527299 (machine translation of the same enclosed herewith).

* cited by examiner

*Primary Examiner* — Renee Claytor
*Assistant Examiner* — Jennifer C Sawyer

(57) ABSTRACT

The present disclosure relates to a method for producing a secondary amine or tertiary amine or mixture thereof in a single reaction step and the use of such amines in various applications including, but not limited to, polyurethane, oil & gas, metalworking, paints and other coatings applications.

6 Claims, No Drawings

METHOD FOR PRODUCING SECONDARY AND TERTIARY AMINES

CROSS-REFERENCE TO RELATED APPLICATION

This application is the National Phase of International Application PCT/US2021/058166 filed Nov. 5, 2021 which designated the U.S. and which claims priority to U.S. Provisional Application No. 63/110,592 filed Nov. 6, 2020. The noted application(s) are incorporated herein by reference.

FIELD

The present disclosure generally relates to a method for producing a low volatile secondary and/or tertiary amines, and in particular, a bis-(N,N-dimethylaminoethoxyethyl) amine and/or an alkylated bis-(N,N-dimethylaminoethoxyethyl)amine, and their use in various applications, including, but not limited to, applications relating to polyurethanes, oil and gas, metalworking, paint and other coating.

BACKGROUND

Polyurethane (PU) flexible foam has the characteristics of light weight, high resilience, good comfort, durability, high sound insulation and high vibration absorption. These materials are widely used in car seats, backrests, headrests, armrests, sound insulation systems and other applications. With the increasing demand for automotive quality and environmental protection, odor and volatile organic compounds (VOC) in PU materials are receiving more and more attention.

In order to improve PU material odor and VOC emission standards, research has intensified in this area during the last decade. Many polyether polyol suppliers have tried to reduce the aldehyde content of the polyether itself while auxiliary manufacturers have also introduced low-volatile catalysts and silicone oils as well as aldehydes scavengers.

The latest low-volatile catalysts launched into the polyurethanes market include alkylated bis-(N,N-dimethylaminoethoxyethyl)amine and, in particular, bis-(N,N-dimethylaminoethoxyethyl)methylamine, which have a relatively high boiling point and are, therefore, commonly referred to as "low volatile catalysts" or "low emission catalysts".

For example, DE2618280 describes for the first time the preparation of bis-(N,N-dimethylaminoethoxyethyl)methylamine and the use of this molecule as a PU catalyst. However, some of the chlorinated sulfur and/or phosphorous based products used in the process described in DE2618280 are extremely toxic, hazardous and dangerous to store, handle or transport. Thus, they are not suitable to be used on an economically viable scale in a chemical process.

More recently, WO2010139521A1 disclosed the first industrial scalable process for the preparation of bis-(N,N-dimethylaminoethoxyethyl)methylamine. This method, as compared to the one described in DE2618280, is free of chlorine, phosphor and/or sulfur in free or bound form, providing a highly pure material after distillation. The method generally includes two or more steps, including reacting N,N-2-dimethylaminoethoxyethanol with ammonia to obtain mainly bis-(N,N-2-dimethylaminoethoxyethyl) amine, which is then methylated into the desired product.

While the method described in WO2010139521 may be suitable for preparing alkylated bis-(N,N-dimethylaminoethoxyethyl)amine catalysts, this method is cumbersome and it would be desirable to develop a new economically viable method that can be used to prepare such catalysts with fewer steps or even as few as a single step.

SUMMARY

The present disclosure provides a method for producing at least one of a secondary amine, a tertiary amine, or a mixture thereof by reacting at least one alcohol represented by formula (1)

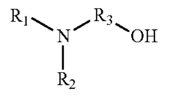

(1)

with at least one amine represented by formula (2)

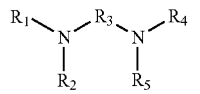

(2)

in the presence of hydrogen and a catalyst wherein each $R_1$ and $R_2$ is independently selected from hydrogen and a $C_1$-$C_4$ alkyl group, each $R_3$ is an alkyl ether moiety independently selected from the group consisting of $—CH_2—CH_2—O—CH_2—CH_2—$, $—CH_2—CH_2—O—CH_2—CH_2—CH_2—$ and $—CH_2—CH_2—CH_2—O—CH_2—CH_2—CH_2—$ and each $R_4$ and $R_5$ are independently selected from hydrogen or a lower alkyl group. The secondary amine or tertiary amine, alone or combined in a mixture, may be useful as a catalyst for producing a polyurethane material or as a component in other applications, such as oil and gas, metalworking, paint and other coating applications.

Thus, in yet another embodiment, there is provided a method of forming a polyurethane material comprising contacting a compound containing an isocyanate functional group and an active hydrogen-containing compound in the presence of the secondary amine, tertiary amine, or mixture thereof as set forth in the present disclosure.

DETAILED DESCRIPTION

The following terms shall have the following meanings:

The term "comprising" and derivatives thereof are not intended to exclude the presence of any additional component, step or procedure, whether or not the same is disclosed herein. In order to avoid any doubt, all compositions claimed herein through use of the term "comprising" may include any additional additive or compound, unless stated to the contrary. In contrast, the term, "consisting essentially of" if appearing herein, excludes from the scope of any succeeding recitation any other component, step or procedure, except those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical objects of the article. By way of example, "an amine" means one amine or more than one amine. The phrases "in one embodiment", "according to one embodiment" and the like generally mean the particular feature, structure, or characteristic following the phrase is included in at least one embodiment of the present disclosure, and may be included in more than one embodiment of the present disclosure. Importantly, such phrases do not necessarily refer to the same aspect. If the specification states a component or feature "may", "can", "could", or "might" be included or have a characteristic, that particular component or feature is not required to be included or have the characteristic.

The term "about" as used herein can allow for a degree of variability in a value or range, for example, it may be within 10%, within 5%, or within 1% of a stated value or of a stated limit of a range.

Values expressed in a range format should be interpreted in a flexible manner to include not only the numerical values explicitly recited as the limits of the range, but to also include all of the individual numerical values or sub-ranges encompassed within that range as if each numerical value and sub-range is explicitly recited. For example, a range such as from 1 to 6, should be considered to have specifically disclosed sub-ranges, such as, from 1 to 3, from 2 to 4, from 3 to 6, etc., as well as individual numbers within that range, for example, 1, 2, 3, 4, 5, and 6. This applies regardless of the breadth of the range.

The terms "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the present disclosure.

Where substituent groups are specified by their conventional chemical formula, written from left to right, they equally encompass the chemically identical substituents that would result from writing the structure from right to left, for example, $—CH_2O—$ is equivalent to $—OCH_2—$.

The term "alkyl group" is inclusive of both straight chain and branched chain, saturated or unsaturated, alkyl groups. Such alkyl groups may have up to 20 carbon atoms unless otherwise specified. In some embodiments, alkyl groups may be lower alkyl groups. The term "lower alkyl" refers to alkyl groups having from 1 to 4 carbon atoms. Examples of lower alkyl groups include, but are not limited to, methyl, ethyl, n-propyl, i-propyl, and butyl groups.

The term "optional" or "optionally" means that the subsequently described event or circumstance may or may not occur, and that the description includes instances where said event or circumstance occurs and instances where it does not.

The term "polyurethane", as used herein, is understood to encompass pure polyurethane, polyurethane polyurea, and pure polyurea.

The term polyurethane "material(s)", as used herein, include rigid foams, flexible foams, semi-rigid foams, integral foams, microcellular elastomers, cast elastomeric foams, polyurethane-isocyanurate foams, reaction injection molded polymers, structural reaction injection molded polymers and the like.

The present disclosure is generally directed to a method for producing at least one of a secondary amine, a tertiary amine, or a mixture thereof by reacting at least one alcohol represented by formula (1)

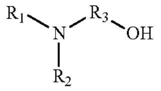

(1)

with at least one amine represented by formula (2)

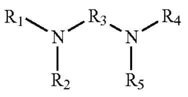

(2)

in the presence of hydrogen and a catalyst where each $R_1$ and $R_2$ is independently selected from hydrogen and a $C_1$-$C_4$ alkyl group, each $R_3$ is an alkyl ether moiety independently selected from the group consisting of $—CH_2—CH_2—O—CH_2—CH_2—$, $—CH_2—CH_2—O—CH_2—CH_2—CH_2—$ and $—CH_2—CH_2—CH_2—O—CH_2—CH_2—CH_2—$ and each $R_4$ and $R_5$ is independently selected from hydrogen or a lower alkyl group.

In one particular embodiment, the method produces at least one of bis-(N,N-dimethylaminoethoxylethyl)amine or bis-(N,N-dimethylaminoethoxyethyl)alkylamine, and in particular bis-(N,N-dimethylaminoethoxyethyl)methylamine. Other embodiments of the bis(N,N-dimethylaminoethoxyethyl)alkylamine include those where the "alkyl" group is an ethyl, butyl, pentyl, or hexyl group.

It has been surprisingly found that the method of the present disclosure can be performed to produce the at least one secondary amine, tertiary, amine or mixture thereof in economically acceptable quantities in a single step as compared to state of the art methods which require multiple steps.

The present disclosure is also directed to polyurethane materials, specifically polyurethane foams (including, for example, rigid, semi-rigid or flexible polyurethane foam), made from a polyurethane formulation comprising the secondary amine, tertiary amine, or mixture thereof as described herein, a compound containing an isocyanate functional group and an active hydrogen-containing compound.

Accordingly, there is provided a method for producing at least one of a secondary amine, a tertiary amine, or a mixture thereof by reacting at least one alcohol represented by formula (1)

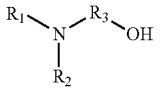

(1)

with at least one amine represented by formula (2)

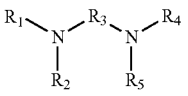

(2)

in the presence of a catalyst where each $R_1$ and $R_2$ is independently selected from a $C_1$-$C_4$ alkyl group, each $R_3$ is an alkyl ether moiety independently selected from the group consisting of —$CH_2$—$CH_2$—O—$CH_2$—$CH_2$—, —$CH_2$—$CH_2$—O—$CH_2$—$CH_2$—$CH_2$— and —$CH_2$—$CH_2$—$CH_2$—O—$CH_2$—$CH_2$—$CH_2$—, and each $R_4$ and $R_5$ is independently selected from hydrogen and a lower alkyl group.

According to one particular embodiment, $R_1$ and $R_2$ are the same. In another embodiment $R_1$ and $R_2$ are independently selected from methyl, ethyl or n-propyl groups, and in particular methyl groups. In another embodiment, each $R_3$ is a —$CH_2$—$CH_2$—O—$CH_2$—$CH_2$— group. In still another embodiment, $R_4$ and $R_5$ are independently selected from hydrogen or a lower alkyl group, and in a particular embodiment the lower alkyl group is a methyl group. In still another embodiment $R_4$ and $R_5$ are the same, and in a particular embodiment a methyl group.

Thus, according to one embodiment, the compound of the at least one amine is selected from one or more of N,N-dimethyl-2-(2-(methylamino)ethoxy)ethan-1-amine ("T3MBAEE"), 2-(2-aminoethoxy)-N,N-dimethylethan-1-amine ("T2MBAEE"), and 2,2'-oxybis(N-methylethan-1-amine) ("T2*MBAEE"), which are represented by formulas (3)-(5), respectively:

(3)

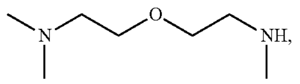

N,N-dimethyl-2-(2-(methylamino)ethoxy)ethan-1-amine (T3MBAEE)

(4)

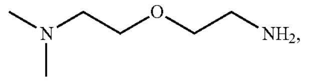

2-(2-aminoethoxy)-N,N-dimethylethan-1-amine (T2MBAEE)

(5)

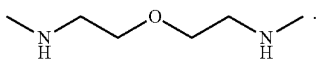

2,2′-oxybix(N-methylethan-1-amine) (T2*MBAEE)

In one particular embodiment, the at least one amine is N,N-dimethyl-2-(2-(methylamino)ethoxy)ethan-1-amine (T3MBAEE). In a further embodiment, the at least one amine is a mixture of T3MBAEE, T2MBAEE, T2*MBAEE and 2,2'-oxybis(N,N-dimethylethan-1-amine) ("T4MBAEE"), wherein T4MBAEE is represented by formula (6):

(6)

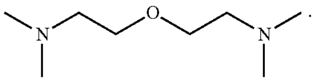

2,2′-oxybis(N,N-dimethylethan-1-amine) (T4MBAEE)

In such an embodiment when the at least one amine is a mixture of T3MBAEE, T2MBAEE, T2*MBAEE, and T4MBAEE, the mixture includes T3MBAEE in an amount of at least 10% by weight, or at least 20% by weight, or at least 30% by weight, or at least 40% by weight or at least 50% by weight, or at least 60% by weight, or at least 70% by weight, or at least 80% by weight or even at least 90% by weight, based on the total weight of the mixture.

In still another embodiment, the at least one alcohol comprises 2-(2-(dimethylamino)ethoxy)ethan-1-ol, which is represented by formula (7) below:

(7)

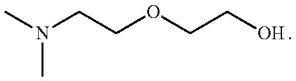

2-(2-(dimethylamino)ethoxy)ethan-1-ol

In a further embodiment, the at least one alcohol comprises at least 90% by weight, or at least 95% by weight or even at least 99% by weight of 2-(2-(dimethylamino)ethoxy)ethan-1-ol.

Thus, according to particular embodiments, there is provided a method for producing a secondary amine comprising bis(N,N-dimethylethoxyethyl)amine by reacting the at least one alcohol and the at least one amine in the presence of hydrogen and a catalyst. In yet another particular embodiment, there is provided a method for producing a tertiary amine comprising bis(N,N-dimethylethoxyethyl)alkylamine, and in particular a bis(N,N-dimethylethoxyethyl)methylamine by reacting the at least one alcohol and the at least one amine in the presence of hydrogen and a catalyst. In still another embodiment, there is provided a method for producing a secondary amine comprising bis(N,N-dimethylethoxyethyl)amine and a tertiary amine comprising bis-(N,N-dimethylaminoethyoxyethyl)amine by reacting the at least one alcohol and the at least one amine in the presence of hydrogen and a catalyst.

In the embodiments above, the method can produce a mixture of secondary amines or a mixture of tertiary amines or a mixture of secondary amines and tertiary amines, such amines may be separated by known means, such as by distillation.

The weight ratio of the compound of at least one alcohol to the at least one amine may range from about 30:70 to about 70:30, or from about 40:60 to about 60:40, or from about 45:55 to about 55:45 or even from about 50:50.

According to one embodiment the catalyst present may be a copper-chromite catalyst. Copper-chromite catalysts are examples of typical oxidic catalysts of Group I B/VI B of Periodic Table of elements, which catalysts are suitable for the reaction of the compounds of the formula (1) and (2) above.

Numerous promoters may be used, mainly comprising elements of the Groups I A and IIA, IV B, IV A, VIII B. Other suitable catalysts for use in the reaction above are supported or non-supported catalysts of the Group of VIII B. Carriers for group VIII B metals are $Al_2O_3$, $SiO_2$, $TiO_2$, activated carbon, etc. Also, some embodiments may add different promoters to such catalysts above, mainly of the Groups I A and II A, IV B, IV A.

In some embodiments, a catalyst load, expressed as LHSV (=liter/liter*h"$^{1}$) based upon the feed of the at least one alcohol, of 0.01 to 2.0, preferably 0.1 to 1 may be used.

According to another embodiment, there is provided a method of forming a polyurethane material comprising contacting a compound containing an isocyanate functional group and an active hydrogen-containing compound in the presence of the secondary amine or tertiary amine or mixture thereof of the present disclosure.

According to another embodiment, the secondary amine or tertiary amine or mixture thereof may be combined with other known secondary/tertiary amine catalysts as well as at least one non-amine. A non-amine catalyst is a compound having catalytic activity for the reaction of an isocyanate group with an active hydrogen-containing compound. Examples of such additional non-amine catalysts include, for example: tertiary phosphines, such as trialkylphosphines and dialkylbenzylphosphines; chelates of various metals, such as those which can be obtained from acetylacetone, benzoylacetone, trifluoroacetyl acetone, ethyl acetoacetate and the like, with metals such as Be, Mg, Zn, Cd, Pd, Ti, Zr, Sn, As, Bi, Cr, Mo, Mn, Fe, Co and Ni; metal carboxylates such as potassium acetate and sodium acetate; acidic metal salts of strong acids, such as ferric chloride, stannic chloride, stannous chloride, antimony trichloride, bismuth nitrate and bismuth chloride; strong bases, such as alkali and alkaline earth metal hydroxides, alkoxides and phenoxides; alcoholates and phenolates of various metals, such as $Ti(OR_6)_4$, $Sn(OR_6)_4$ and $Al(OR_6)_3$ where $R_6$ is alkyl or aryl, and the reaction products of the alcoholates with carboxylic acids, beta-diketones and 2-(N,N-dialkylamino) alcohols; alkaline earth metal, Bi, Pb, Sn or Al carboxylate salts; and tetravalent tin compounds, and tri- or pentavalent bismuth, antimony or arsenic compounds.

The secondary amine or tertiary amine or mixture thereof and optional non-amine catalyst may be used in a catalytically effective amount to catalyze the reaction between a compound containing an isocyanate functional group and an active hydrogen-containing compound for making rigid, semi-rigid or flexible polyurethane foam or other polyurethane materials. A catalytically effective amount of the secondary amine, tertiary amine or mixture thereof and optional non-amine catalyst above may range from about 0.01-15 parts per 100 parts of active hydrogen-containing compound, and in some embodiments from about 0.05-12.5 parts per 100 parts of active hydrogen-containing compound, and in even further embodiments from about 0.1-7.5 parts per 100 parts of active hydrogen-containing compound, and yet in even further embodiments from about 0.5-5 parts per 100 parts of active hydrogen-containing compound. In one particular embodiment, the amount of the secondary amine or tertiary amine or mixture thereof and optional non-amine may range from about 0.1-3 parts per 100 parts of active hydrogen-containing compound.

In one embodiment, the step of reacting the at least one alcohol and the at least one amine comprises heating a mixture of the at least one alcohol, the at least one amine, and a catalyst at a temperature ranging from 80° C. to 250° C. at a liquid load ranging from 0.01 to 1 kg/hour of the at least one alcohol and the at least one amine to 1 liter of the catalyst. In one embodiment, the alcohol, amine, and catalyst are reacted at a pressure range of 10 to 200 bar.

In one embodiment, the compound containing an isocyanate functional group is a polyisocyanate and/or an isocyanate-terminated prepolymer.

Polyisocyanates include those represented by the general formula $Q(NCO)_a$ where a is a number from 2-5, such as 2-3 and Q is an aliphatic hydrocarbon group containing 2-18 carbon atoms, a cycloaliphatic hydrocarbon group containing 5-10 carbon atoms, an araliphatic hydrocarbon group containing 8 to 13 carbon atoms, or an aromatic hydrocarbon group containing 6 to 15 carbon atoms.

Examples of polyisocyanates include, but are not limited to, ethylene diisocyanate; 1,4-tetramethylene diisocyanate; 1,6-hexamethylene diisocyanate; 1,12-dodecane diisocyanate; cyclobutane-1,3-diisocyanate; cyclohexane-1,3- and 1,4-diisocyanate, and mixtures of these isomers; isophorone diisocyanate; 2,4- and 2,6-hexahydrotoluene diisocyanate and mixtures of these isomers; dicyclohexylmethane-4,4'-diisocyanate (hydrogenated MDI, or HMDI); 1,3- and 1,4-phenylene diisocyanate; 2,4- and 2,6-toluene diisocyanate and mixtures of these isomers (TDI); diphenylmethane-2,4'-and/or -4,4'-diisocyanate (MDI); naphthylene-1,5-diisocyanate; triphenylmethane-4,4',4"-triisocyanate; polyphenyl-polymethylene-polyisocyanates of the type which may be obtained by condensing aniline with formaldehyde, followed by phosgenation (crude MDI); norbornane diisocyanates; m- and p-isocyanatophenyl sulfonylisocyanates; perchlorinated aryl polyisocyanates; modified polyisocyanates containing carbodiimide groups, urethane groups, allophnate groups, isocyanurate groups, urea groups, or biruret groups; polyisocyanates obtained by telomerization reactions; polyisocyanates containing ester groups; and polyisocyanates containing polymeric fatty acid groups. Those skilled in the art will recognize that it is also possible to use mixtures of the polyisocyanates described above.

Isocyanate-terminated prepolymers may also be employed in the preparation of the polyurethane material. Isocyanate-terminated prepolymers may be prepared by reacting an excess of polyisocyanate or mixture thereof with a minor amount of an active-hydrogen containing compound as determined by the well-known Zerewitinoff test.

In another embodiment, the active hydrogen-containing compound is a polyol. Polyols suitable for use in the present disclosure include, but are not limited to, polyalkylene ether polyols, polyester polyols, polymer polyols, a non-flammable polyol such as a phosphorus-containing polyol or a halogen-containing polyol. Such polyols may be used alone or in suitable combination as a mixture.

Polyalkylene ether polyols include poly(alkylene oxide) polymers, such as poly(ethylene oxide) and polypropylene oxide) polymers, and copolymers with terminal hydroxyl groups derived from polyhydric compounds, including diols and triols; for example, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane, and similar low molecular weight polyols.

Polyester polyols include, but are not limited to, those produced by reacting a dicarboxylic acid with an excess of a diol, for example, adipic acid with ethylene glycol or butanediol, or reaction of a lactone with an excess of a diol such as caprolactone with propylene glycol.

In addition to polyalkylene ether polyols and polyester polyols, polymer polyols are also suitable for use in the present disclosure. Polymer polyols are used in polyurethane materials to increase resistance to deformation, for example, to improve the load-bearing properties of the foam or material. Examples of polymer polyols include, but are not limited to, graft polyols or polyurea modified polyols (Polyharnstoff Dispersion polyols). Graft polyols comprise a triol in which vinyl monomers are graft copolymerized. Suitable vinyl monomers include, for example, styrene, or acrylonitrile. A polyurea modified polyol is a polyol containing a polyurea dispersion formed by the reaction of a diamine and a diisocyanate in the presence of a polyol. A variant of polyurea modified polyols are polyisocyanate polyaddition (PIPA) polyols, which are formed by the in situ reaction of an isocyanate and an alkanolamine in a polyol.

The non-flammable polyol may, for example, be a phosphorus-containing polyol obtainable by adding an alkylene oxide to a phosphoric acid compound. A halogen-containing polyol may, for example, be those obtainable by ring-opening polymerization of epichlorohydrin or trichlorobutylene oxide.

The method of producing the polyurethane material may also be conducted in the presence of one or more halogenated olefin compounds that serve as a blowing agent. The halogenated olefin compound comprises at least one haloalkene (e.g., fluoroalkene or chlorofluoroalkene) comprising from 3 to 4 carbon atoms and at least one carbon-carbon double bond. Suitable compounds may include hydrohaloolefins such as trifluoropropenes, tetrafluoropropenes (e.g., tetrafluoropropene (1234)), pentafluoropropenes (e.g., pentafluoropropene (1225)), chlorotrifloropropenes (e.g., chlorotrifloropropene (1233)), chlorodifluoropropenes, chlorotrifluoropropenes, chlorotetrafluoropropenes, hexafluorobutenes (e.g., hexafluorobutene (1336)), or combinations thereof. In certain embodiments, the tetrafluoropropene, pentafluoropropene, and/or chlorotrifloropropene compounds have no more than one fluorine or chlorine substituent connected to the terminal carbon atom of the unsaturated carbon chain (e.g., 1,3,3,3-tetrafluoropropene (1234ze); 1,1,3,3-tetrafluoropropene, 1,2,3,3,3-pentafluoropropene (1225ye), 1,1,1-trifluoropropene, 1,2,3,3,3-pentafluoropropene, 1,1,1,3,3-pentafluoropropene (1225zc), 1,1,2,3,3-pentafluoropropene (1225yc), (Z)-1,1,1,2,3-pentafluoropropene (1225yez), 1-chloro-3,3,3-trifluoropropene (1233zd), 1,1,1,4,4,4-hexafluorobut-2-ene (1336mzzm), or combinations thereof).

Other blowing agents that may be used alone or in combination with the halogenated olefin compounds described above include air, nitrogen, carbon dioxide, hydrofluorocarbons ("HFCs"), alkanes, alkenes, mono-carboxylic acid salts, ketones, ethers, or combinations thereof. Suitable HFCs include 1,1-difluoroethane (HFC-152a), 1,1,1,2-tetrafluoroethane (HFC-134a), pentafluoroethane (HFC-125), 1,1,1,3,3-pentafluoropropane (HFC-245fa), 1,1,1,3,3-pentaflurobutane (HFC-365mfc) or combinations thereof. Suitable alkanes and alkenes include n-butane, n-pentane, isopentane, cyclopentane, 1-pentene, or combinations thereof. Suitable mono-carboxylic acid salts include methyl formate, ethyl formate, methyl acetate, or combinations thereof. Suitable ketones and ethers include acetone, dimethyl ether, or combinations thereof.

In addition, the method of producing the polyurethane material may also be conducted in the presence of one or more auxiliary components. Examples of auxiliary components include, but are not limited to, cell stabilizers, surfactants, chain extenders, pigments, fillers, flame retardants, thermally expandable microspheres, water, thickening agents, smoke suppressants, reinforcements, antioxidants, UV stabilizers, antistatic agents, infrared radiation absorbers, dyes, mold release agents, antifungal agents, biocides or any combination thereof.

Cell stabilizers may include, for example, silicon surfactants or anionic surfactants. Examples of suitable silicon surfactants include, but are not limited to, polyalkylsiloxane, polyoxyalkylene polyol-modified dimethylpolysiloxane, alkylene glycol-modified dimethylpolysiloxane, or any combination thereof.

Suitable surfactants (or surface-active agents) include emulsifiers and foam stabilizers, such as silicone surfactants known in the art, for example, polysiloxanes, as well as various amine salts of fatty acids, such as diethylamine oleate or diethanolamine stearate, as well as sodium salts of ricinoleic acids.

Examples of chain extenders include, but are not limited to, compounds having hydroxyl or amino functional groups, such as glycols, amines, diols, and water. Further non-limiting examples of chain extenders include ethylene glycol, propylene glycol, 1,4-butanediol, 1,3-butanediol, 1,5-pentanediol, 1,6-hexanediol, 1,10-decanediol, 1,12-dodecanediol, ethoxylated hydroquinone, 1,4-cyclohexanediol, N-methylethanolamine, N-methylisopropanolamine, 4-aminocyclo-hexanol, 1,2-diaminoethane, or any mixture thereof.

Pigments may be used to color code the polyurethane materials during manufacture, to identify product grade, or to conceal yellowing. Pigments may include any suitable organic or inorganic pigments. For example, organic pigments or colorants include, but are not limited to, azo/diazo dyes, phthalocyanines, dioxazines, or carbon black. Examples of inorganic pigments include, but are not limited to, titanium dioxide, iron oxides or chromium oxide.

Fillers may be used to increase the density and load bearing properties of the polyurethane foam or material. Suitable fillers include, but are not limited to, barium sulfate, carbon black or calcium carbonate.

Flame retardants can be used to reduce flammability. For example, such flame retardants include, but are not limited to, chlorinated phosphate esters, chlorinated paraffins or melamine powders.

Thermally expandable microspheres include those containing a (cyclo)aliphatic hydrocarbon. Such microspheres are generally dry, unexpanded or partially unexpanded microspheres consisting of small spherical particles with an average diameter of typically 10 to 15 micron. The sphere is formed of a gas proof polymeric shell (e.g. consisting of acrylonitrile or PVDC), encapsulating a minute drop of a (cyclo)aliphatic hydrocarbon, e.g. liquid isobutane. When these microspheres are subjected to heat at an elevated temperature level (e.g. 150° C. to 200° C.) sufficient to soften the thermoplastic shell and to volatilize the (cyclo) aliphatic hydrocarbon encapsulated therein, the resultant gas expands the shell and increases the volume of the microspheres. When expanded, the microspheres have a diameter 3.5 to 4 times their original diameter as a consequence of which their expanded volume is about 50 to 60 times greater than their initial volume in the unexpanded state. Examples of such microspheres are the EXPANCEL®-DU microspheres which are marketed by AKZO Nobel Industries of Sweden.

The methods for producing a polyurethane material from a polyurethane formulation according to the present disclosure are well known to those skilled in the art and can be found in, for example, U.S. Pat. Nos. 5,420,170, 5,648,447, 6,107,359, 6,552,100, 6,737,471 and 6,790,872, the contents of which are hereby incorporated by reference. Various types of polyurethane materials can be made, such as rigid foams, flexible foams, semi-rigid foams, integral foams, microcellular elastomers, cast elastomeric foams, polyurethane-isocyanurate foams, reaction injection molded polymers, structural reaction injection molded polymers and the like.

According to one embodiment, the polyurethane material according to the present disclosure is a flexible polyurethane foam having a compressive stress at 10% compression or compressive strength according to DIN 53 421/DIN EN ISO 604 of 15 kPa and less, preferably 1 to 14 kPa and in particular 4 to 14 kPa.

According to another embodiment the polyurethane material according to the present disclosure is a semi-rigid polyurethane foam having a compressive stress at 10% compression according to DIN 53 421/DIN EN ISO 604 of greater than 15 kPa to less than 80 kPa. According to DIN ISO 4590, semi-rigid polyurethane foams and flexible polyurethane foams according to the present disclosure may have an open cell of preferably greater than 85%, particularly preferably greater than 90%.

According to another embodiment, the polyurethane material according to the present disclosure is a rigid polyurethane foam having a compressive stress at 10% compression of greater than or equal to 80 kPa, preferably greater than or equal to 120 kPa, particularly preferably greater than or equal to 150 kPa. Furthermore, the rigid polyurethane foam according to DIN ISO 4590 has a closed cell of greater than 80%, preferably greater than 90%.

In another embodiment, the polyurethane material is an elastomeric polyurethane foam which is understood to mean a polyurethane foam in accordance with DIN 7726 which, after brief deformation by 50% of the thickness in accordance with DIN 53 577, have no permanent deformation over 2% of their original thickness after 10 minutes. These can be a rigid polyurethane foam, a semi-rigid polyurethane foam or a flexible polyurethane.

In a further embodiment, the polyurethane material according to the present disclosure is an integral polyurethane foam according to DIN 7726 with an edge zone which, due to the molding process, have a higher density than the core. The total bulk density averaged over the core and the peripheral zone is preferably above 100 g L. Integral polyurethane foams in the sense of this disclosure can also be rigid polyurethane foams, semi-rigid polyurethane foams or flexible polyurethane foams.

In one embodiment, the polyurethane material according to the present disclosure is a polyurethane foam with an average density of 20 g/L to 850 g/L, preferably a polyurethane rigid foam or a flexible polyurethane foam or a rigid polyurethane foam, particularly preferably an elastomeric flexible polyurethane foam, a rigid polyurethane foam or an elastomeric integral polyurethane foam.

In one particular embodiment, the polyurethane material according to the invention is a polyurethane foam with an average density of 20 to 850 g/L, preferably a semi-rigid polyurethane foam or a flexible polyurethane foam, particularly preferable an elastomeric flexible polyurethane foam, a semi-rigid polyurethane foam or an elastomeric integral polyurethane foam.

The elastomeric integral polyurethane foam preferably has a density of 150 g/L to 500 g/L averaged over the core and the edge zone. The flexible polyurethane foam preferably has an average density of 10 g/L to 100 g/L. The semi-rigid polyurethane foam preferably has an average density of 70 g/L to 150 g/L In a further embodiment, the polyurethane foam according to the present disclosure is a solid polyurethane with a density of preferably more than 850 g/L, preferably 900 g/L to 1400 g/L and particularly preferably 1000 g/L to 1300 g/L. A solid polyurethane is obtained essentially without the addition of a blowing agent. A small amount of blowing agent, for example water, which is contained in the polyols for production reasons, is not considered a blowing agent. The polyurethane formulation for producing the compact polyurethane foam preferably contains less than 0.2% by weight, particularly preferably less than 0.1% by weight and in particular less than 0.05% by weight of water.

In one particular embodiment, the polyurethane material is a rigid, semi-rigid or flexible foam prepared by bringing together at least one polyol and at least one polyisocyanate in the presence of the at least one secondary amine or tertiary amine of the present disclosure to form a reaction mixture and subjecting the reaction mixture to conditions sufficient to cause the polyol to react with the polyisocyanate. The polyol, polyisocyanate and the at least one secondary amine and tertiary amine may be heated prior to mixing them and forming the reaction mixture. In other embodiments, the polyol, polyisocyanate, build-in amine catalyst and sulfonic acid ester are mixed at ambient temperature (for e.g. from about 15° C.-40° C.) and heat may be applied to the reaction mixture, but in some embodiments, applying heat may not be necessary. The polyurethane foam may be made in a free rise (slabstock) process in which the foam is free to rise under minimal or no vertical constraints. Alternatively, molded foam may be made by introducing the reaction mixture in a closed mold and allowing it to foam within the mold. The particular polyol and polyisocyanate are selected with the desired characteristics of the resulting foam. Other auxiliary components useful in making polyurethane foams, such as those described above, may also be included to produce a particular type of foam.

The polyurethane materials produced may be used in a variety of applications including, but not limited to, in vehicle interior and exterior parts of means of transport such as ships, airplanes, trucks, cars or buses, particularly preferably cars or buses and in particular cars. The interior of cars and buses is referred to below as the automotive interior part. A flexible polyurethane foam can be used as a seat cushion, a semi-rigid polyurethane foam as back-foaming of door side elements or instrument panels, an integral polyurethane foam as a steering wheel, shift button. The polyurethane foam may also be used in bed liners, dashboards, door panels. In other embodiments, the polyurethane foam may be used as: a precoat; a backing material for carpet; building composites; insulation; spray foam insulation; applications requiring use of impingement mix spray guns; urethane/urea hybrid elastomers; integral skin foams; rigid spray foams; rigid pour-in-place foams; coatings; adhesives; sealants; filament winding; and other polyurethane composite, foams, elastomers, resins, and reaction injection molding (RIM) applications. In other embodiments, the may be used as a component for use in other compositions, such as oil & gas, metalworking, paints and other coatings compositions.

The present disclosure will now be further described with reference to the following non-limiting example.

EXAMPLES

Example 1

A 1000 ml stainless steel adiabatic downflow reactor was charged with 2 kg of commercial copper-chromite catalyst (HyMax® 250, from Clariant). The head of the continuous reactor system was connected with an inlet line and a feed pump for the raw materials shown below which were previously mixed at a ratio 50:50 wt %. The reactor effluents were taken off at the bottom of the reactor, depressurized, degassed and collected for analysis and further use. The tables below show the raw materials stream composition, all running conditions and the effluents composition.

| Raw Material Composition | |
|---|---|
| | (wt %) |
| Compound (2) | |
| T4MBAEE | 3.77 |
| T3MBAEE | 45.78 |
| T2MBAEE + T2*MBAEE | 0.45 |
| Compound (1) | |
| 2-(2-(dimethylamino)ethoxy)ethan-1-ol | 50.00 |

| Reaction conditions | Unit | Run 1 | Run 2 |
|---|---|---|---|
| Reactor Temperature | ° C. | 180 | 190 |
| Reactor Pressure | Bar | 10 | 10 |
| Raw Material Feed | g/h | 200 | 200 |

| Product Composition (area %) Compound | Run 1 | Run 2 |
|---|---|---|
| Trimethylamine | 1.19 | 0.71 |
| N-methyl morpholine | 7.77 | 6.09 |
| T4MBAEE | 16.41 | 16.36 |
| T3MBAEE | 16.32 | 7.96 |
| T2MBAEE + T2*MBAEE | 0.18 | 0.06 |
| 2-(2-(dimethylamino)ethoxy)ethan-1-ol | 26.93 | 22.81 |
| Diethylene glycol | 0.26 | 0.24 |
| bis-(N,N-2-dimethylaminoethoxyethyl)amine | 2.49 | 3.33 |
| bis-(N,N-dimethylaminoethoxyethyl)methylamine | 21.64 | 36.69 |
| Unidentified compounds | 6.81 | 5.75 |

While the foregoing is directed to various embodiments of the present disclosure, other and further embodiments of the disclosure may be devised without departing from the basic scope thereof, and the scope thereof is determined by the claims that follow.

What is claimed is:

1. A method for producing at least one of a secondary amine comprising bis(N,N-dimethylaminoethoxyethyl) amine, a tertiary amine comprising bis(N,N-dimethylaminoethoxyethyl)alkylamine, or a mixture thereof by reacting at least one alcohol represented by formula (1)

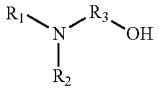

(1)

with at least one amine represented by formula (2)

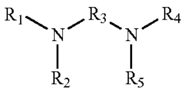

(2)

in the presence of hydrogen and a catalyst in a single step, wherein each $R_1$ and $R_2$ is independently selected from hydrogen and a $C_1$-$C_4$ alkyl group, each $R_3$ is an alkyl ether moiety independently selected from the group consisting of $-CH_2-CH_2-O-CH_2-CH_2-$, $-CH_2-CH_2-O-CH_2-CH_2-CH_2-$ and $-CH_2-CH_2-CH_2-O-CH_2-CH_2-CH_2-$ and each $R_4$ and $R_5$ is independently selected from hydrogen or a lower alkyl group having from 1 to 4 carbon atoms.

2. The method of claim 1, wherein the catalyst comprises a copper-chromite catalyst.

3. The method of claim 2, wherein the at least one alcohol comprises 2-(2-(dimethylamino) ethoxy) ethan-1-ol.

4. The method of claim 3, wherein the at least one amine comprises N,N-dimethyl-2-(2-(methylamino)ethoxy)ethan-1-amine.

5. The method of claim 4, wherein the at least one amine further comprises 2,2'-oxybis(N,N-dimethylethan-1-amine).

6. The method of claim 1 wherein the weight ratio of the at least one alcohol to the at least one amine is in a range from about 30:70 to about 70:30.

* * * * *